(12) United States Patent
Zhang et al.

(10) Patent No.: US 9,925,220 B2
(45) Date of Patent: Mar. 27, 2018

(54) METHOD OF EXPANDING DOUBLE NEGATIVE T CELLS

(71) Applicant: University Health Network, Toronto (CA)

(72) Inventors: Li Zhang, Toronto (CA); Mei Han, Toronto (CA); Pouneh Dokouhaki, Oakville (CA)

(73) Assignee: University Health Network, Toronto, Ontario (CA)

( * ) Notice: Subject to any disclaimer, the term of this patent is extended or adjusted under 35 U.S.C. 154(b) by 318 days.

(21) Appl. No.: 14/674,548

(22) Filed: Mar. 31, 2015

(65) Prior Publication Data
US 2016/0045550 A1   Feb. 18, 2016

Related U.S. Application Data

(63) Continuation of application No. 12/093,492, filed as application No. PCT/CA2006/001870 on Nov. 20, 2006, now Pat. No. 9,018,004.

(60) Provisional application No. 60/737,759, filed on Nov. 18, 2005.

(51) Int. Cl.
*C12N 5/0783* (2010.01)
*A61K 35/17* (2015.01)

(52) U.S. Cl.
CPC ............ *A61K 35/17* (2013.01); *C12N 5/0636* (2013.01); *C12N 2501/23* (2013.01); *C12N 2501/2302* (2013.01); *C12N 2501/2304* (2013.01); *C12N 2501/515* (2013.01)

(58) Field of Classification Search
None
See application file for complete search history.

(56) References Cited

U.S. PATENT DOCUMENTS

| | | |
|---|---|---|
| 5,312,733 A | 5/1994 | MacLeod |
| 5,985,656 A | 11/1999 | Strober |
| 6,537,812 B1 | 3/2003 | Bell et al. |
| 6,905,681 B1 | 6/2005 | June et al. |
| 6,953,576 B2 | 10/2005 | Zhang et al. |
| 7,175,843 B2 | 2/2007 | June et al. |
| 2003/0157060 A1 | 8/2003 | Bell et al. |
| 2003/0170238 A1 | 9/2003 | Gruenberg et al. |

FOREIGN PATENT DOCUMENTS

WO         01/75072       10/2001

OTHER PUBLICATIONS

Suggitt et al. (Clinical Cancer Research, vol. 11, 971-981, Feb. 1, 2005).*
Igney et al., Cancer Immunol Immunother (2005) 54: 1127-1136.*
Renga et al. (Annals of Oncology 14: 1177-1184, 2003).*
Bui et al., J Immunol 176, 905-913 (2006) (Year: 2006).*
SChwinn et al., Int J Cancer 124, 1594-1604 (2009) (Year: 2009).*
Bender, A. and Kabelitz, D., "CD4-CD8—Human T Cells: Phenotypic Heterogeneity and Activation Requirements of Freshly Isolated "Double Negative" T Cells", Cellular Immunology, 1990, vol. 128, No. 2, p. 542-554.
Chatterjee et al., "Idiotypic antibody immunotherapy of cancer", Cancer Immunol. Immuother., 1994, v. 38, p. 75-82.
Chen, Wenhao et al., "The role and mechanism of double negative regulatory T cells in the suppression of immune responses" Cellular & Molecular Immunology, 2004 p. 328-335, vol. 1, No. 5.
Dermer, G.B., "Another Anniversary for the War on Cancer", Biotechnology 12:320, 1994.
Dixon, J.F.P. et al., "Activation of Human T Lymphocytes by Crosslinking of Anti-CD3 Monoclonal Antibodies", Journal of Leukocyte Biology, 46 :214-220 (1989).
Dokouhaki et al., "Adoptive Immunotherapy of cancer using ex vivo expanded human ••δ ells: A new approach". Cancer Letters 297 (2010) 126-136.
Fischer, Karin et al, "Isolation and characterization of human antigen-specific TCR• β+ CD4-CD8-double-negative regulatory T cells", Blood, American Society of Hematology, 2005, p. 2828-2835, vol. 105, No. 7.
Gessner, J.E. et al., "The IgG Fc receptor family", Ann Hematol (1998) 76 :231-248.
Hertel-Wulff, Birgit et al., "In vivo propagation and cloning of murine natural suppressor (NS) cells", Journal of Immunology, 1984, p. 2791-2796, vol. 133, No. 5.
Kakkanaiah, V.N. et al., "CD4-CD8—Thymocytes from MRL-Ipr/Ipr Mice Exhibit Abnormal Proportions of AlphaBeta- and GammaDelta-TCR+ Cells and Defective Responsiveness When Activated through the TCR", Cellular Immunology, 1991, vol. 137, No. 2, p. 269-282.
Klingemann, H.G., "An Hematotherapist's Point of View: Cellular Therapy of Cancer with Natural Killer Cells: Will It Ever Work?" J of Hematotherapy and Stem Cell Research, 2001, v. 10, p. 23-26.
Kunzmann et al., "Anti-lymphoma effect of GammaDelta T cells", Leukemia & Lymphoma, May 2005, 46(5):671-680.
Schaberg et al., "Lymphocyte Subsets in Peripheral Blood and Smoking Habits", Lung (1997) 175:387-394.

(Continued)

*Primary Examiner* — Zachary S Skelding
(74) *Attorney, Agent, or Firm* — Bereskin & Parr LLP/S.E.N.C.R.L., s.r.l.; Micheline Gravelle

(57) ABSTRACT

A method of expanding double negative T cells in culture is described. The method comprises (a) providing a starting sample comprising DN T cells or precursors thereof; (b) substantially depleting $CD8^+$ and $CD4^+$ T cells from the starting sample; (c) culturing the sample from step (b) with an immobilized T cell mitogen in a culture medium comprising an agent that can stimulate DN T cell growth (d) washing the cells obtained in step (c) and resuspending in a culture medium comprising the agent without the T cell mitogen; and (e) washing the cells obtained in step (d) and resuspending in a culture medium comprising the agent and a soluble T cell mitogen. The DN T cells obtained by the method are useful in a variety of applications including the treatment of cancer, infectious diseases, graft versus host disease and autoimmune disease.

20 Claims, 9 Drawing Sheets

(56) References Cited

OTHER PUBLICATIONS

Sussman J.J. et al., "Activation of T Lymphocytes for the Adoptive Immunotherapy of Cancer", Annals of Surgical Oncology, 1994, v. 1, p. 296-306.
Thornton et al., "CD4+ CD25+ Immunoregulatory T Cells Suppress Polyclonal T Cell Activation In Vitro by Inhibiting Interleukin 2 Production", The Journal of Experimental Medicine, Jul. 20, 1998; 188(2):287-296.
Yamaguchi et al., "A simple method for the propagation and purification of GammaDelta T cells from the peripheral blood of glioblastoma patients using solid-phase anti-CD3 antibody and soluble IL-2". Journal of Immunological Methods 205 (1997) 19-28.
Young, K.J. et al., "Antitumor Activity Mediated by Double-Negative T Cells", Cancer Research, 2003, vol. 63, p. 8014-8021.
Zhang, Zhu-Xu et al., "Identification of a previously unknown antigen-specific regulatory T cell and its mechanism of suppression", Nature Medicine, 2000, p. 782-789, vol. 6, No. 1.
Zhang, Zhu-Xu, et al., "Double-Negative T Cells, Activated by Xenoantigen, Lyse Autologous B and T Cells Using a Perforin/Granzyme-Dependent, Fas-Fas Ligand-Independent Pathway", The Journal of Immunology, 2006, vol. 177, No. 10, p. 6920-6929.

\* cited by examiner a b

H460

H460 + CD8

H460 + DNT

METHOD OF EXPANDING DOUBLE NEGATIVE T CELLS

RELATED APPLICATIONS

This application is a continuation of U.S. patent application Ser. No. 12/093,492 filed Sep. 24, 2008 (allowed), which is a national phase entry application of PCT/CA2006/001870 filed Nov. 20, 2006 (which designated the U.S.) which claims the benefit of U.S. provisional patent application Ser. No. 60/737,759 filed Nov. 18, 2005. All of the prior applications are incorporated herein by reference in their entirety.

FIELD OF THE INVENTION

The present invention relates to a method of expanding double negative T cells ex vivo.

BACKGROUND OF THE INVENTION

Adoptive cancer immunotherapy involves isolation, ex vivo activation and expansion of immune cells, and subsequent injection into patients with cancer. Since Rosenberg et al first introduced adoptive immunotherapy for the treatment of human cancers (Rosenberg et al. 1985; Rosenberg et al. 1988), several types of immune cells, including lymphokine activated killer cells (LAK), $CD8^+$ cytotoxic T lymphocytes (CTL), natural killer (NK) cells, NK T cells and tumor infiltrating lymphocytes (TIL) have been used in clinical trials (Vemrneris et al. 2002; Toh et al. 2005; Leemhuis et al. 2005; Yee et al. 2002; Dudley and Rosenberg 2003; Dudley et al. 2005). Currently the transfer of ex vivo activated and expanded autologous tumor specific $CD8^+$ CTLs may induce objective clinical responses in significant number of patients (Gattinoni et al. 2005; Rosenberg, Yang, and Restifo 2004; Dudley and Rosenberg 2003; Childs and Barrett 2004; Riddell 2004; Yee et al. 2002) and are considered the most effective approach to immunotherapy (Pure, Allison, and Schreiber 2005). However, this treatment is severely limited by the need to identify relevant tumor antigens. Moreover, cancer relapse occurs even after repeated injections (Meidenbauer et al. 2003). This probably is because many of the in vitro cultured CTLs die within a few hours after adoptive transfer and most do not survive for more than a few days (Gattinoni et al. 2005; Riddell 2004; Speiser and Romero 2005; Zhang, Miller, and Zhang 1996; Khan et al. 1999). This approach can also result in severe autoimmune disease in treated patients (Dudley and Rosenberg 2003). Adoptive transfer of activated allogeneic lympocytes can mount effective anti-tumor responses, but the infused allogeneic cells can also attack host tissue and organs causing graft versus host disease (GVHD). Recent studies, including the inventors' work, have shown in both animal models and cancer patients that adoptive transfer of allogeneic lymphocytes recognizing either host minor histocompatibility antigens (MiHA) or single MHC class I antigens can mediate effective anti-tumor activities towards hematopoetic malignancies without causing GVHD (Young et al. 2003b; Perreault and Brochu 2002; Fontaine et al. 2001; Marijt et al. 2003). Because identifying a single class I, particularly a dominant MiHA that is present in patients but not in donors, is a difficult task, its clinical application to patients is complex. The current goal of adoptive cancer immunotherapy is to develop novel strategies allowing the generation of a large number of T cells that can persist and migrate to tumor sites, and effectively eliminate tumor cells without causing GVHD or autoimmune disease.

The majority of T cells in human peripheral blood express either CD4 or CD8 molecules. Approximately 1-3% of them express CD3 but lack CD4 and CD8 co-receptors. Based on the expression of the natural killer (NK) cell markers, these cells can be divided further into 2 subpopulations: NKT cells which express NK cell surface markers such as CD56 and CD16, and double negative (DN) cells which do not express these NK markers. Previously the inventors have demonstrated in mouse models that DN T cells express a unique set of cell surface markers and a cytokine profile that distinguishes them from previously described lymphocytes (Zhang et al. 2000). Unlike CD4 or CD8 T cells, infusion of in vitro activated allogeneic DN T cells did not cause GVHD. Furthermore, the injected allogeneic DN T cells can also prevent CD8 T cell-induced GVHD in recipients. Moreover, this treatment can prevent death in more than 75% of the recipients that were inoculated with a lethal dose of autologous A20 lymphoma cells either systemically or locally (Young et al. 2003b; Young et al. 2001).

Several studies have shown that autologous and syngeneic $CD8^+$ T cells can be manipulated to induce anti-tumor responses (Lan et al. 2001; Dudley et al. 2002; Dudley and Rosenberg 2003). Although injection of allogeneic DN T cells does not appear to cause GVHD in mice (Young et al. 2003a), using autologous DN T cells that are activated by the patient's tumor antigens have following advantages over use of allogeneic T cells: 1) Injection of autologous cells does not have risk of causing GVHD or transmitting other disease; 2) They may allow induction of controlled and specific immune responses tailored for the individual cancer patient; 3) Autologous cells are easier to be applied to phase I and II clinical trails.

Human DN T cells were recently characterized. They display similar characteristics as those found in mouse DN T cells in terms of cell surface marker expression, cytokine profile, and mechanisms of action (Fischer et al. 2005; Zhang et al. 2000). However, the role of human DN T cells in tumor immunity has not been investigated previously due to the limited number of DN T cells that can be obtained.

In view of the foregoing, there is a need in the art to develop a method for expanding double negative T cells in culture.

SUMMARY OF THE INVENTION

The inventors have developed a protocol by which human double negative (DN) T cells can be purified from peripheral blood and expanded ex vivo. The anti-tumor effect of these ex vive expanded human DN T cells was compared with $CD8^+$ cytotoxic T lymphocytes (CTLs) obtained from the same donors. The inventors have found that human DN T cells are more effective than CTLs in inhibiting tumor growth in vitro. More importantly, when adoptively transferred into immunodeficient mice, DN T cells showed much more potent anti-tumor effect than $CD8^+$ T cells.

The present invention provides a method of expanding double negative (DN) T cells in a sample comprising:
  (a) providing a starting sample comprising DN T cells or precursors thereof;
  (b) substantially depleting $CD8^+$ and $CD4^+$ T cells from the starting sample;
  (c) culturing the sample from step (b) with an immobilized T cell mitogen in a culture medium comprising an agent that can stimulate the growth of DN T cells;

(d) washing the cells obtained in step (c) and resuspending in a culture medium comprising the agent without the T cell mitogen; and (e) washing the cells obtained in step (d) and resuspending in a culture medium comprising the agent and a soluble T cell mitogen.

The DN T cells obtained by the method of the invention can be used in a variety of experimental, therapeutic and commercial applications.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

Figure 1:
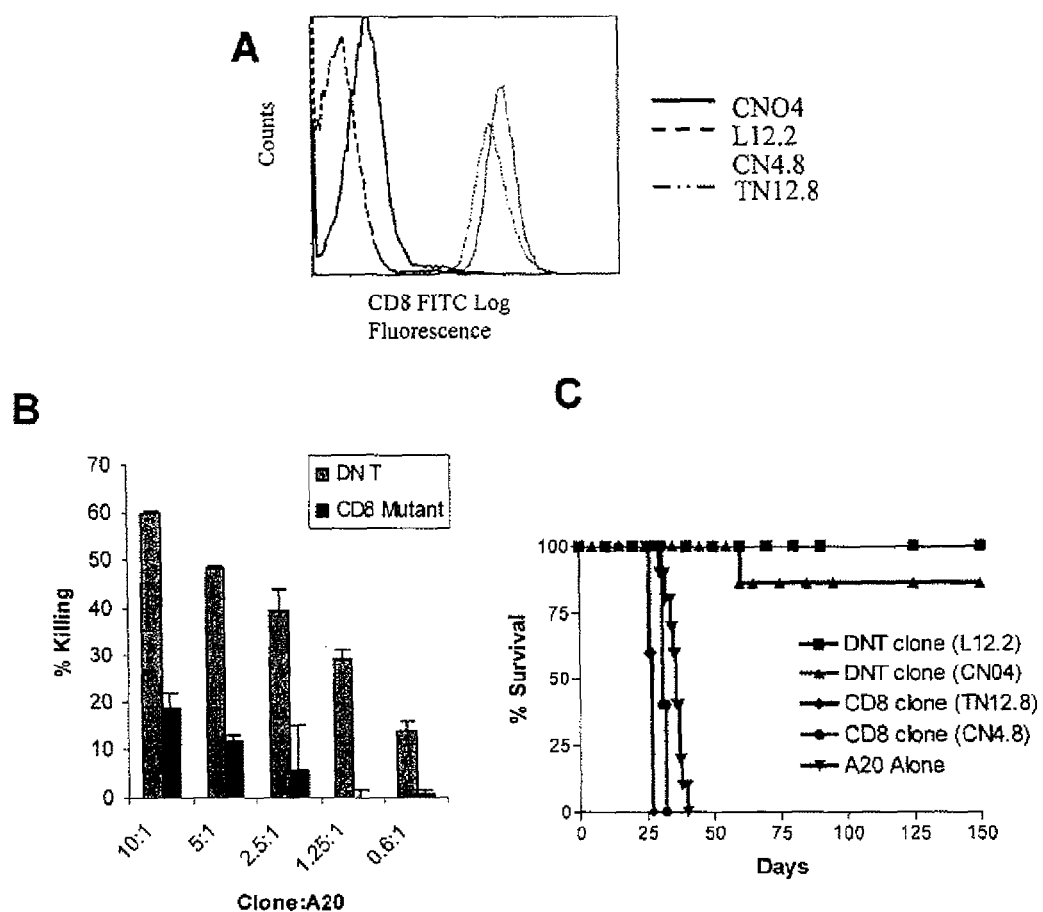
FIG. 1A-C are graphs showing that DN T cell clones, but not their CD8$^+$ mutants, can kill A20 tumor cells in vitro and eradicate lymphoma after adoptive transfer.

I. Method of Expanding DN T Cells

As mentioned previously, the present inventors have developed a method for expanding double negative T cells in vitro. Accordingly, the present invention provides a method of expanding double negative (DN) T cells in a sample comprising:

(a) providing a starting sample comprising DN T cells or precursors thereof;

(b) substantially depleting CD8$^+$ and CD4$^+$ T cells from the starting sample;

(c) culturing the sample from step (b) with an immobilized T cell mitogen in a culture medium comprising an agent that can stimulate DN T cell growth;

(d) washing the cells obtained in step (c) and resuspending in a culture medium comprising the agent without the T cell mitogen; and (e) washing the cells obtained in step (d) and resuspending in a culture medium comprising the agent and a soluble T cell mitogen.

The term "double negative T cell" or "DN T cell" means a T lymphocyte that expresses CD3 but lacks the cell surface expression of CD4, CD8 molecules as well as CD16, a common marker for neutrophils, macrophages and NK cells. The DN T cells will express a T-cell receptor (TCR) which can be either the $\alpha\beta$ or the $\gamma\delta$ TCR. A population of DN T cells expanded by the method of the invention can include a mixture of both $\alpha\beta^+$ and $\gamma\delta^+$ T cells. In a preferred embodiment, the DN T cell is a human cell.

The starting sample can be any biological sample that contains double negative T cells or precursors thereof. Such samples include but are not limited to, fresh or cryopreserved blood, bone marrow, lymphoid tissue, thymus, liver, spleen, lymph node tissue, tumor tissue, fetal tissue and fractions or enriched portions thereof.

In a preferred embodiment, the starting sample is blood, preferably human blood, more preferably human peripheral blood.

Prior to culturing the starting sample or fraction thereof, the starting sample is substantially depleted of both CD4$^+$ and CD8$^+$ T cells. By "substantially" it is meant that the majority of these cells are depleted but does not exclude that a small portion of these cells remain. The sample may be depleted of these cell types using techniques known in the art. Specifically, antibodies that bind to the CD8 and CD4 cells to be depleted but not to the double negative T cells can be added to the starting sample. In a preferred embodiment, labelled antibodies that specifically bind to CD4 and CD8 are added to the sample. Once the starting sample has been depleted of CD4$^+$ and CD8$^+$ T cells, the method of the invention can be continued immediately or the sample can be frozen and stored for later use. As such the expansion of the DN T cells can be initiated from a frozen sample at such a time when the DN cells are needed.

The sample that has been substantially depleted of CD4$^+$ and CD8$^+$ cells is cultured in a culture medium containing an immobilized T cell mitogen as well as an agent that can stimulate DN T cell growth.

The immobilized T cell mitogen can be any agent that can stimulate double negative T cells including, but not limited to, antibodies that bind to CD3 or T cell receptor as well as lectins including the plant lectin concanavalin A (ConA) and phytohaemagglutinin (PHA) or any compound that can stimulate DN T cells expansion such as, but not limited to, IPP, Pamidronate and Zoledronate. Preferably, the T cell mitogen is an antibody to CD3 such as OKT3.

The T cell mitogen can be immobilized using techniques known in the art. Preferably, the T cell mitogen is coated on to a solid support including but not limited to, microwell plates, culture dishes, culture bags or flasks. Preferably, the T cell mitogen is an immobilized anti-CD3 antibody, more preferably immobilized on microwell plates.

The agent that can stimulate DN T cell growth can be any suitable agent and is preferably a cytokine such as an interleukin. Preferably, the cytokine comprises interleukin-2 (IL-2), interleukin-4 (IL-4), interleukin-7 (IL-7), interleukin-15 (IL-15), interleukin-12 (IL-12) or mixtures of two or more of these In a specific embodiment, IL-2 and IL-4 are used.

The concentration of the agent will be suitable to promote the expansion of the double negative cells. Preferably, cytokines are administered in a range from about 0.1 ng/mL to about 50 ng/mL. More specifically, the IL-2 is administered in an amount of 1-20 ng/mL and IL-4 is administered in an amount of 0-1 ng/mL.

The culture medium can be any medium suitable for the culture of T cells including, but not limited to, RPMI medium, serum free media, X-VIVO10 and X-VIVO15. The culture medium will preferably contain other suitable agents including fetal bovine serum (FBS) and antibiotics.

In one embodiment, the cells will be stimulated with antigen and cytokines prior to culturing with the agent that can stimulate DN T cell growth and the immobilized T cell mitogen. In the preparation of anti-tumor DN T cells, inactivated tumor cells or peptides from tumor specific or tumor associated antigens may be used. In the clinical setting, cells from the patient's tumor can be used to prepare autologous DN T cells from the patient's blood.

The cells are preferably cultured in any of the steps (b)-(d) for a period of time ranging from 1 to about 10 days. Preferably, each step is conducted for about 3-7 days, more preferably, 3-4 days.

To increase the purity of the DN T cells prepared by the method of the invention, the sample obtained after step (e) can be further enriched by depleting any cells that are not DN T cells. In a specific embodiment, the sample is further depleted of $CD8^+$, $CD4^+$ and $CD56^+$ cells.

The purity of the DN T cells isolated by the present method can be confirmed using techniques known in the art such as flow cytometry.

II. Uses of DN T Cells

The present invention also includes the use of the double negative T cells obtained by the method of invention in any and all applications.

As shown in the Examples, the double negative T cells expanded by the method of invention have strong anti-tumor effects. Accordingly, in one embodiment the present invention provides a method of treating a tumor comprising administering an effective amount of a double negative T cell obtained by the method of the present invention to an animal in need thereof. The present invention also includes a use of an effective amount of a double negative T cell obtained by the method of the present invention for treating a tumor. The present invention further includes a use of an effective amount of a double negative T cell obtained by the method of the present invention in the manufacture of a medicament for treating a tumor.

The term "effective amount" as used herein means an amount effective, at dosages and for periods of time necessary to achieve the desired result, e.g. to treat a tumor.

The term "animal" as used herein includes all members of the animal kingdom, including humans. In a preferred embodiment, the animal is human.

The term "treating" includes, but is not limited to, alleviation or amelioration of one or more symptoms or conditions of a disease or condition (such as cancer, autoimmune disease, allergy, infection etc.), diminishment of extent of disease, stabilized state of disease, preventing spread of disease, delaying or slowing of disease progression, and amelioration or palliation of the disease state, remission whether detectable or undetectable and/or prolonged survival as compared to expected survival if not receiving treatment.

In the treatment of a tumor or cancer, the tumor that can be treated can be any tumor that is amenable to treatment with double negative T cells either alone or in combination with other treatment such as surgery, radiation therapy or chemotherapy etc. Examples of tumors that may be treated according to the present invention include, but are not limited to, leukemias including chronic myelogenous leukemia, acute myelogenous leukemia, acute lymphoblastic leukemia, and T cell and B cell leukemias, lymphomas (Hodgkins and non-Hodgkins), lymphoproliferative disorders, plasmacytomas, histiocytomas, melanomas, adenomas, sarcomas, carcinomas of solid tissues, hypoxic tumours, squamous cell carcinomas, genitourinary cancers such as cervical and bladder cancer, breast and lung cancers, hematopoietic cancers, head and neck cancers, and nervous system cancers.

The invention also includes other therapeutic uses of the DN T cells of the invention such as the treatment of infectious diseases and for modulating an immune response for example in the treatment of autoimmune diseases, allergies, graft rejection and graft versus host disease. In such cases, the method of preparing the DN T cells can include adding the appropriate infectious agent, allergen cells or tissues as the antigen.

Accordingly, in one embodiment the present invention provides a method of treating an infectious disease comprising administering an effective amount of a double negative T cell obtained by the method of the present invention to an animal in need thereof. The present invention also includes a use of an effective amount of a double negative T cell obtained by the method of the present invention for treating an infectious disease. The present invention further includes a use of an effective amount of a double negative T cell obtained by the method of the present invention in the manufacture of a medicament for treating an infectious disease.

In a further embodiment, the present invention provides a method of modulating an immune response comprising administering an effective amount of a double negative T cell obtained by the method of the present invention to an animal in need thereof. The present invention also includes a use of an effective amount of a double negative T cell obtained by the method of the present invention for modulating an immune response. The present invention further includes a use of an effective amount of a double negative T cell obtained by the method of the present invention in the manufacture of a medicament for modulating an immune response.

In one embodiment, the DN T cells are used to treat an autoimmune disease. Autoimmune diseases that may be treated according to the present invention include, but are not limited to, diabetes, arthritis, multiple sclerosis, lupus erythematosus, inflammatory bowel disease, dermatitis, meningitis, thrombotic thrombocytopenic purpura, Sjögren's syndrome, encephalitis, uveitis, leukocyte adhesion deficiency, rheumatic fever, Reiter's syndrome, progressive systemic sclerosis, primary biliary cirrhosis, necrotizing vasculitis, myasthenia gravis, polymyositis, sarcoidosis, granulomatosis, vasculitis, pernicious anemia, CNS inflammatory disorder, antigen-antibody complex mediated diseases, autoimmune haemolytic anemia, Hashimoto's thyroiditis, Graves disease, habitual spontaneous abortions, Raynaud's syndrome, glomerulonephritis, dermatomyositis, chronic active hepatitis, celiac disease, tissue specific autoimmunity, degenerative autoimmunity delayed hypersensitivities, autoimmune complications of AIDS, atrophic gastritis, ankylosing spondylitis and Addison's disease.

In another embodiment, the DN T cells can be used to treat graft versus host disease wherein the immune cells in the transplant mount an immune attack on the recipient's immune system. This can occur when the tissue to be transplanted contains immune cells such as when bone marrow or lymphoid tissue is transplanted when treating leukemias, aplastic anemias and enzyme or immune deficiencies, for example.

In a further embodiment, the DN T cells can be used to treat an allergic reaction. In an allergic reaction, the immune system mounts an attack against a generally harmless, innocuous antigen or allergen. Allergies that may be prevented or treated using the methods of the invention include, but are not limited to, hay fever, asthma, atopic eczema as well as allergies to poison oak and ivy, house dust mites, bee pollen, nuts, shellfish, penicillin and numerous others.

The DN T cells prepared by the method of the invention may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. The compositions may be administered in a convenient manner preferably by injection such as intravenous, subcutaneous, intramuscular, etc.

The compositions described herein can be prepared by per se known methods for the preparation of pharmaceutically acceptable compositions which can be administered to subjects, such that an effective quantity of the cells is combined in a mixture with a pharmaceutically acceptable vehicle. Suitable vehicles are described, for example, in Remington's Pharmaceutical Sciences (Remington's Pharmaceutical Sciences, 20th ed., Mack Publishing Company, Easton, Pa., USA 2000). On this basis, the compositions include, albeit not exclusively, solutions of the substances in association with one or more pharmaceutically acceptable vehicles or diluents, and contained in buffered solutions with a suitable pH and iso-osmotic with the physiological fluids.

An effective amount of the composition may vary according to factors such as the disease state, age, sex, and weight of the individual, and the ability of the cells to elicit a desired response in the individual. Dosage regime may be adjusted to provide the optimum therapeutic response. For example, several divided doses may be administered daily or the dose may be proportionally reduced as indicated by the exigencies of the therapeutic situation.

The pharmaceutical compositions of the invention may include other active agents that are useful in treating the disease or condition to be treated. For example, in the treatment of a tumor, other anti-cancer agents may be administered either in the same composition or in a separate composition.

The following non-limiting examples are illustrative of the present invention:

EXAMPLES

Example 1

Murine DN Cells

The inventors have generated a panel of mouse DN T cell clones. During long-term cultivation, several natural mutant T cell clones arose which express CD8 (FIG. 1A). In FIG. 1A, $L^{d-}$ DN T cell clones CN04 and L12.2 and their natural mutants CN4.8 and TN12.8 were stained with CD8-FITC, and analyzed by flow cytometry. Both mutant clones are $CD8^+$. The mutant clones have reduced cytotoxicity to A20 tumor in vitro (FIG. 1B). In FIG. 1B, DN T cell clone CN04 and its CD8 mutant clone CN48 were used as effector cells at ratios as indicated. $L^{d+}$ A20 tumour cells were used as targets. Specific lysis of the target cells was measured in a cytotoxic assay. While a single infusion of DN T cell clones can prevent recipient tumor development from a lethal injection of lymphoma cells, adoptive transfer of the same number of $CD8^+$ mutant clones have no protective effect (FIG. 1C). In FIG. 1C, (B6×BALB/c)F1 mice ($L^{d+}$) were infused with $10^5$/mouse A20 tumor cells either alone or together with 5×105 DN T cell clones or their $CD8^+$ mutants as indicated. Percent tumour-free survival in each group is shown. Each group contains 5-12 mice.

Figure 2:
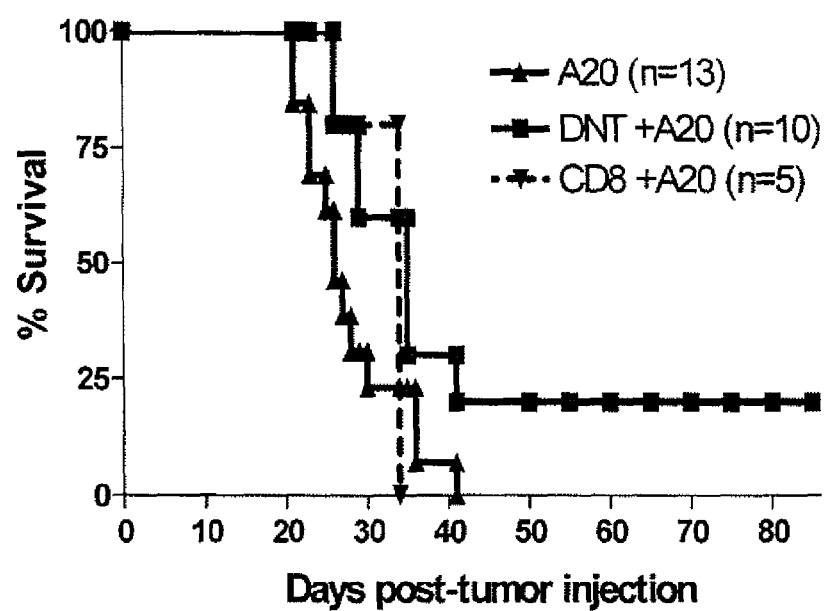
FIG. 2 is a graph showing in vitro activated DN T cells can inhibit tumor progression after adoptive transfer.

To investigate whether DN T cells that are activated in vitro by allogeneic cells can inhibit progression of established tumor, naïve (B6×BALB/c)F1 mice were injected with $10^5$ A20 B lymphoma cells. 3 days after tumor inoculation, each mouse was injected with either $10^6$ in vitro activated DN T or CD8 T cells. Mice that were injected with A20 alone were used as controls. Percent tumor free survival is shown. Injection of DN T cells resulted in significantly prolong tumor free survival compared to those injected with tumor alone or CD8 T cells (P<0.05) (FIG. 2).

Furthermore, the inventors have demonstrated that DN T cells are more resistant to apoptosis than CD8 T cells both in vitro and in vivo (Khan et al. 1999; Marra et al. 2004), another characteristic in which DN T cells may be superior to $CD8^+$ T cells for adoptive cellular therapy.

Figure 3:
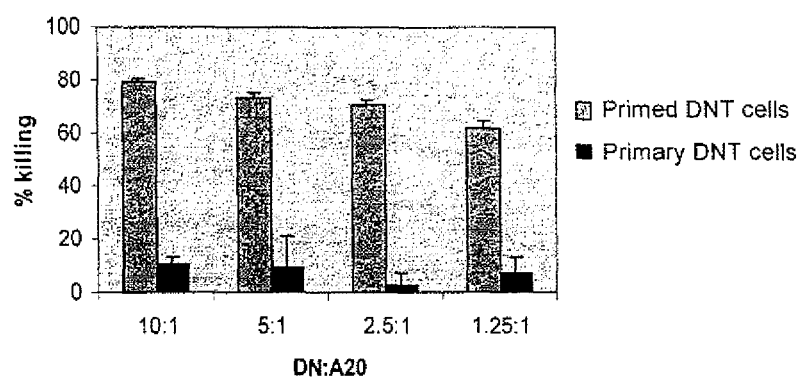
FIG. 3 is a graph showing in vitro primed but not naïve DN T cells cells can kill autologous tumor cells.

The inventors found in mice that, although naïve DN T cells could not kill syngeneic A20 tumor cells, stimulation of purified DN T cells with 1% paraformaldehyde-fixed-A20 cells leads to the expansion and effective killing of syngeneic A20 cells in vitro (FIG. 3). In FIG. 3, DN T cells were purified from naïve (B6×Balb/c)$_{F1}$ mice and used either immediately or after 3 days of stimulation with 1% PFA fixed autologous A20 tumor cells in a cytotoxicity assay as effector cells. Viable A20 tumour cells were used as targets at the indicated ratios. Results shown are the percent specific killing of A20 cells±SD, and are representative of 2 independent experiments each with 3 replicates. This finding suggests the possibility of using in vitro manipulated autologous DN T cells as a novel adoptive cancer therapy.

The inventors have demonstrated in mouse models that infusion of in vitro activated allogeneic DN T cells not only did not cause GVHD but can also prevent CD8 T cells-induced GVHD in recipients (Young et al. 2003b; Young et al. 2001; Young et al. 2003a). Furthermore, this treatment can prevent death in more than 75% of the recipients that were challenged with a lethal dose of autologous A20 lymphoma cells either given systemically or locally (Young et al. 2003b; Young et al. 2001). The inventors also found that DN T cells can be activated, expanded and cloned by in vitro stimulation with allogeneic cells in the presence of exogenous IL-2 and IL-4 (Zhang et al. 2000; Ford et al. 2002). Both in vitro activated DN T cells and their clones can kill tumor cells that express the alloantigen used for DN T cell activation (Young et al. 2003b). Furthermore, in vitro activated allogeneic DN T cells significantly inhibited tumor progression and increased the percentage of tumor-free survival when compared with the CD8 T cells (manuscript in preparation). Taken together, these results demonstrate in mice that, unlike CD4 or CD8 T cells, adoptive transfer of allogeneic DN T cells leads to tumor regression without causing GVHD. This finding opened a new window of using DN T cells as a novel adoptive cancer immunotherapy.

The inventors have shown that in vitro activated DN T cells and their clones can kill tumor cells in vitro. Furthermore, in vitro activated allogeneic DN T cells significantly inhibited tumor progression and increased the percentage of tumor-free survival. Taken together, these results demonstrate in mice that, unlike CD4 or CD8 T cells, adoptive transfer of allogeneic DN T cells leads to tumor regression without causing GVHD.

Similar to $CD4^+CD25^+$ T regulatory cells, DN T cells have potent immune regulatory function, including prolongation of skin and cardiac allo and xenograft survival and inhibition of GVHD (Zhang et al. 2000; Young et al. 2002; Young and Zhang 2002; Young et al. 2003a; Chen et al. 2003; Chen et al. 2005; Young et al. 2001; Ford et al. 2002). DN T cells also play a part in autoimmune and infectious diseases (Priatel, Utting, and Teh 2001; Johansson and Lycke 2003). In tumor immunity, however, DN T cells seem to play a different role than $CD4^+CD25^+$ Treg cells. Most studies have shown that $CD4^+CD25^+$ T cells are detrimental to anti-tumor responses due to their suppression of the function of tumor-infiltrating CTLs (Turk et al. 2004; Viguier et al. 2004; Zou 2005). Poorer prognosis and reduced survival are associated with higher numbers of $CD4^+CD25^+$ T in cancer patients (Sasada et al. 2003; Curiel et al. 2004; Blattman and Greenberg 2004). In contrast, the inventors have demonstrated both in mouse models and in humans (see Example 2) that DN T cells have potent anti-tumor activity in vitro and in vivo.

Example 2

Human DN Cells

Figure 4:
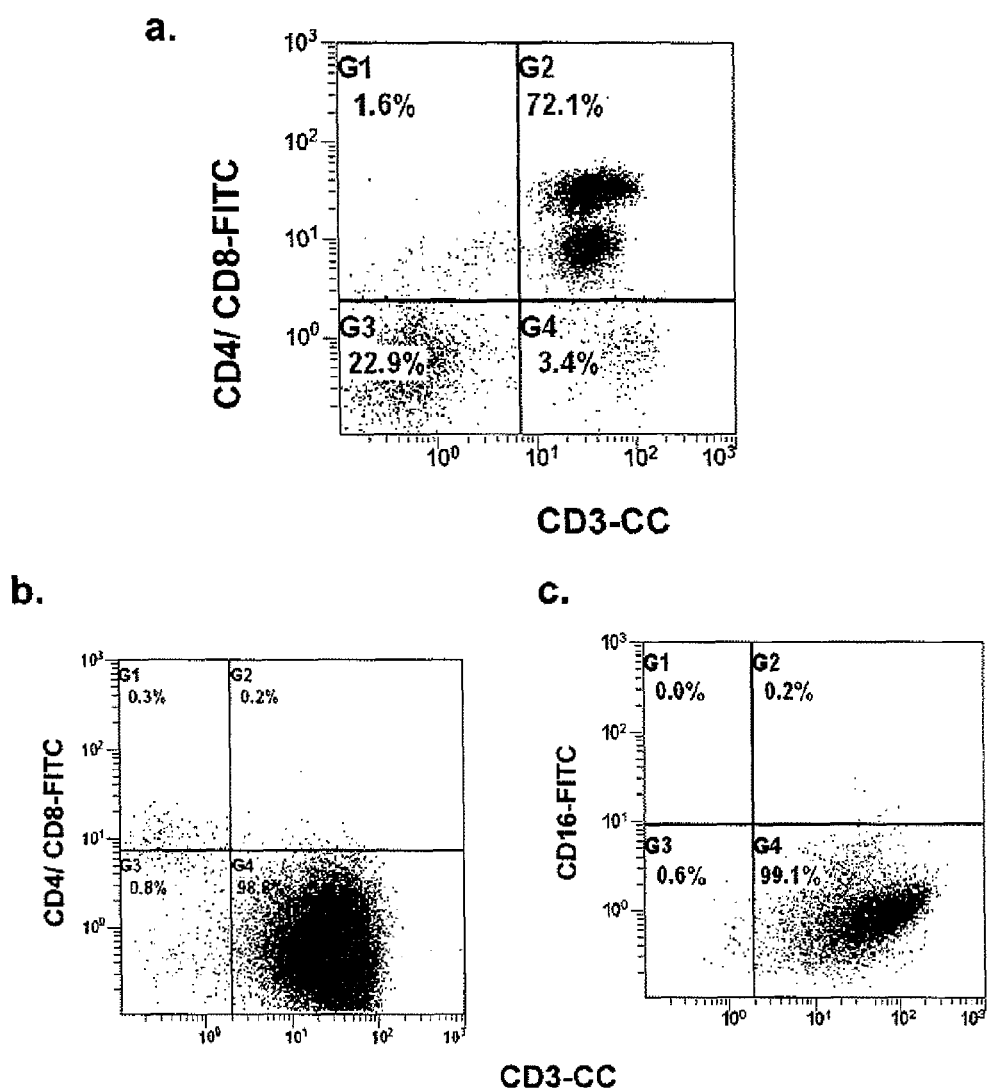
FIGS. 4A-C show the phenotype and percentage of human DN T cells before and after ex vivo expansion.

The population of DN T cells in human peripheral blood is very low (FIG. 4A). To determine whether human DN T cells can be used as a novel cancer adoptive immunotherapy, the inventors developed a protocol by which human DN T cells can be expanded ex vivo. Peripheral blood samples were collected from healthy individuals and the red blood cells were lysed. The remaining PBMC were stained with CD3-Cy-Chrone, CD4-FITC and CD8-FITC. Percentage of $CD3^+CD4^-CD8^-$ T cells in PBMC is shown in G4 region of FIG. 4A. Erythrocytes and CD4, CD8 T cells were depleted using the Human CD4/CD8 depletion cocktail kit (Stem Cell Technologies). The residual DN T cell enriched population was then cultured in anti-CD3 mAb pre-coated 24-well plates for 3 days in the presence of recombinant human interleukin-2 (rhIL-2, 50 U/mL) and rhIL-4 (30 U/mL). Activated T cells were washed and cultured for another 4 days in the presence rhIL-2 and rhIL-4. On day 7, viable cells were split and cultured in fresh media supplemented with rhIL-2, rhIL-4 and soluble anti-CD3 mAb for another 3 days. On day 10 viable cells were collected and aliquots were stained with CD3-PE, CD4-FITC, CD8-FITC and CD56-FITC. Anti-FITC magnetic beads were used to deplete the residual $CD4^+$, $CD8^+$ T cells as well as $CD56^+$ NK cells. Based on 18 experiments that were performed so far, on average, the inventors were able to obtain $1-2 \times 10^8$ DN T cells from 20 mL blood with >95% viability and purity. Percentages of $CD3+CD4^-CD8^-$ T cells and DN T cells ($CD3^+CD4^-CD8^-CD16^-$) are shown in G4 regions of FIG. 4B and FIG. 4C, respectively. The success in obtaining large numbers of highly purified viable human DN T cells makes it possible to use these cells for adoptive cancer immunotherapy.

Figure 5:
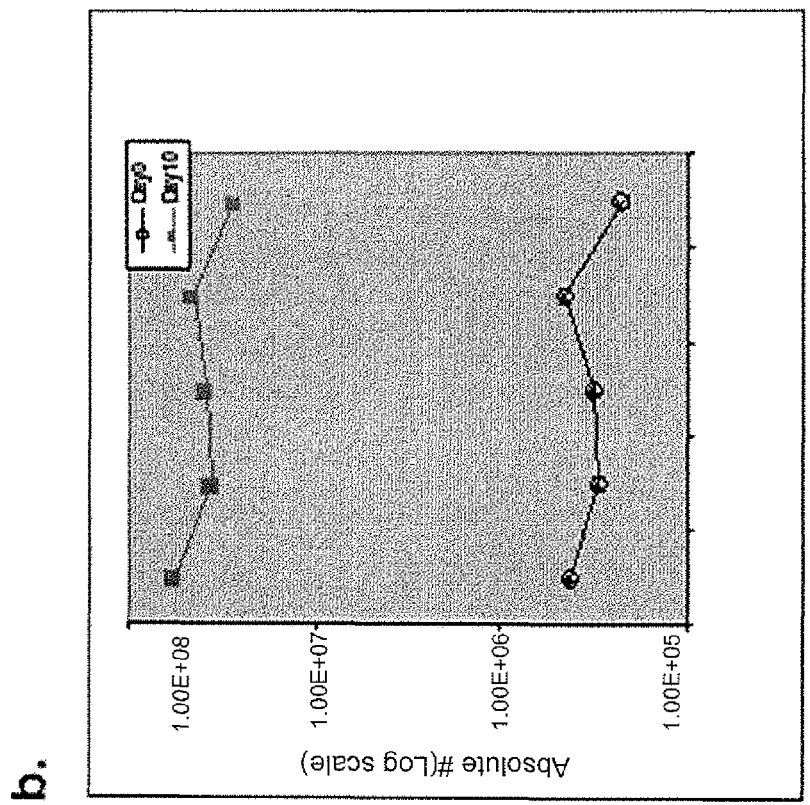
FIGS. 5A and B are graphs showing ex vivo expansion of DN T cells in 5 donors.
Figure 5:
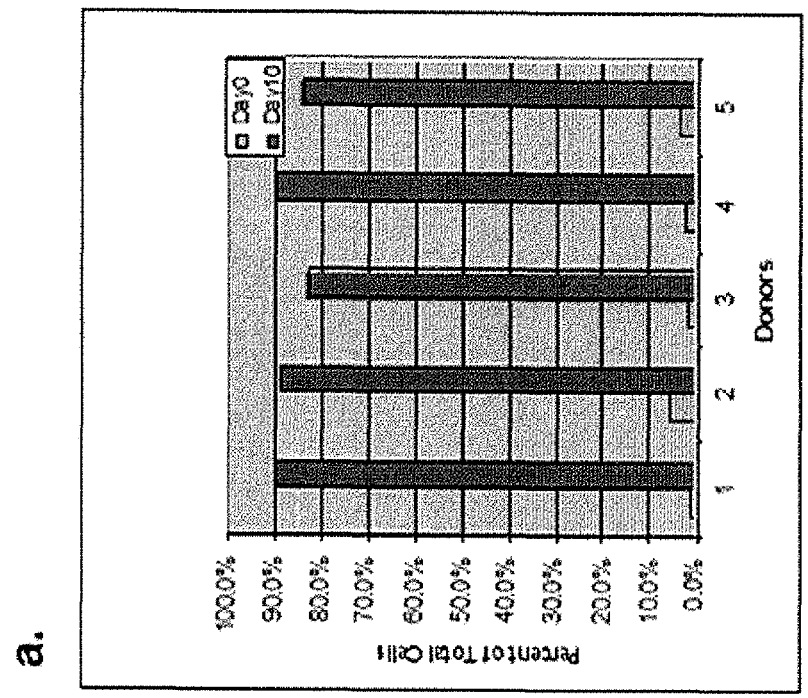

FIG. 5 demonstrates the expansion of DN cells from both healthy donors and cancer patients. Five to ten ml of whole blood was collected from either healthy donors or lung cancer patients in heparinized tubes. $CD4^+$ $CD8^+$ T cells were depleted by Rosetting with RBCs using Rossettsep® kit (Stemcell Technologies Inc) per manufacturer's instructions. Briefly, the blood sample was labelled with anti-human CD4 and CD8 depletion cocktail and incubated for 20 minutes at room temperature, then the blood was diluted 1:1 with Phosphate Buffered Saline (PBS) containing 2% Fetal Bovine Serum (FBS) and layered on equal volume of density gradient medium (Ficol-Hypaque) in a 50 ml conical tube. After centrifugation at 1200×g for 20 minutes, CD4 CD8-depleted PBMC were collected at the interface of ficoll and plasma and washed three times with PBS+2% FBS. The cells were then cultured with the concentration of 0.5-1.0E+ 06 cells per ml in each well of 24-well plate that had been already coated with 5 µg/ml of anti-CD3 monoclonal antibody (clone OKT3) in the presence of RPMI culture medium containing 10% FBS, 50 µM 2-ME, 100 units/ml penicillin, 100 µg/ml streptomycin, 0.1 ng/ml IL-4 and 50 IU/ml IL-2 at 37° C. and 5% CO2 for 3 days. Following the first phase of T cell receptor crosslinking and T cell stimulation, the cells were washed with full medium, transferred from each well of 24-well plate to one well of 6-well plate and continued to culture with the same conditions (full RPMI plus 10% FBS, 0.1 ng/ml IL-4 and 50 IU/ml IL-2) for 4 additional days. On day 7, cells were washed, counted and cultured in fresh full medium in the presence of 0.1 µg/ml soluble anti-CD3 antibody (clone OKT3) plus cytokines. After 3 days, DN T cells were harvested, counted and checked for viability by trypan blue exclusion. An aliquote of the cells were stained with monoclonal antibodies against CD3e, CD4, CD8, CD16 surface markers to check for the purity of DN T cells. Percentages of DN T cells in the total population before and at the end of 10 day culture for 5 healthy donors were shown in FIG. 5A and the total number and yield of DN T cells at the beginning and after 10 days of culture are shown in FIG. 5B.

Figure 6:
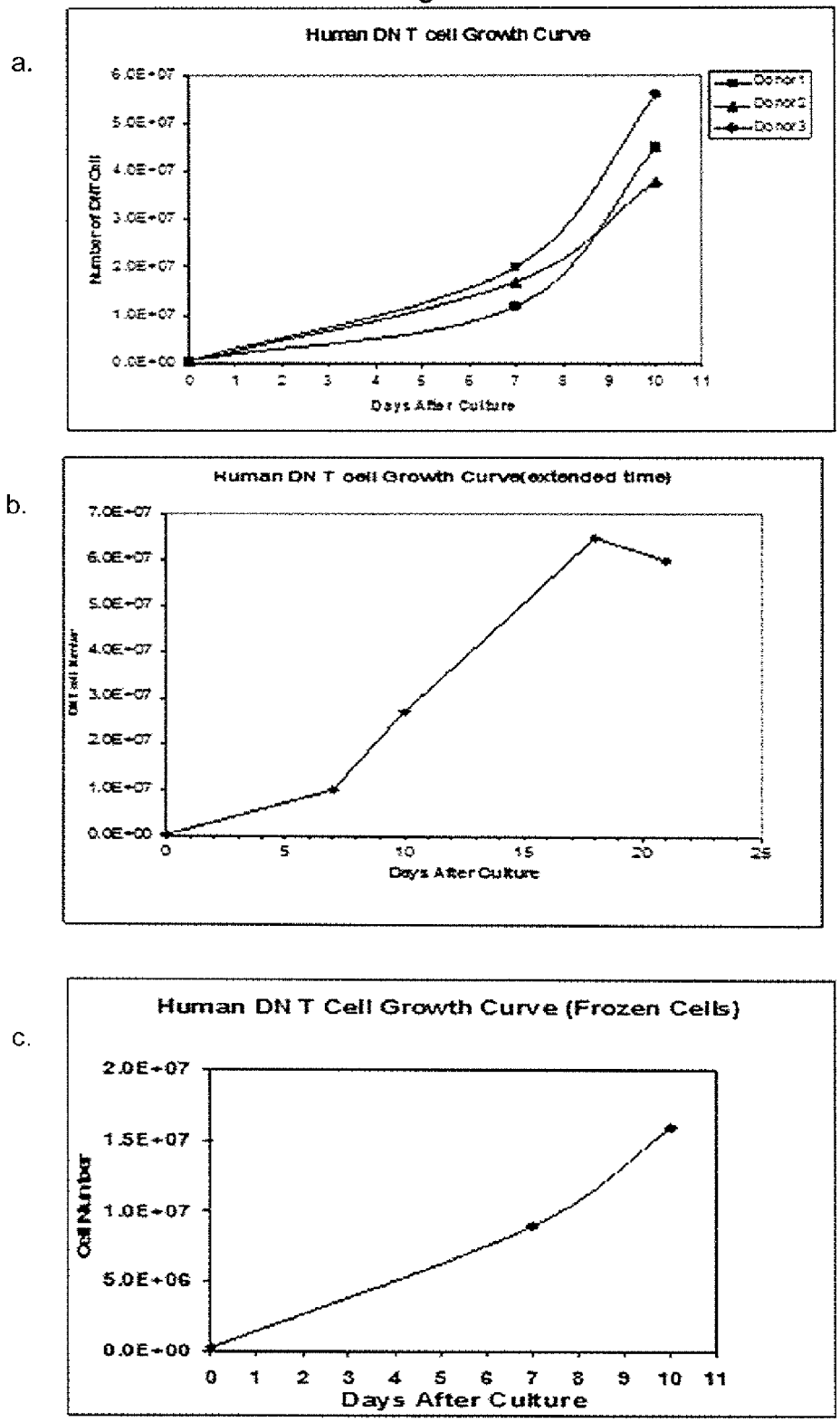
FIGS. 6A-C are graphs showing the growth curve of DN T cells in healthy donors.

FIG. 6 shows the growth curve of DN T cells in healthy donors. DN T cells were cultured as described in FIG. 5. The count and viability of DN T cells present in the culture were checked by trypan blue exclusion method and confirmed by staining with monoclonal antibodies against surface markers and flow cytometry at days 0, 3, 7 and 10. DN T cells were expanded steadily from day 0 to day 7 as they comprised 50-60% of total cells at this time point but the growth rate of DN T cells compared to other T cells present in the culture showed tremendous increase from day 7 to day 10 after the second round of TCR stimulation by anti-CD3 antibody. By day 10, nearly 90% of total cells were DN T cells and they expanded by more than 100 folds (FIG. 6A). When extending the culture period from 10 days to 3 weeks in full RPMI plus 10% FBS, 50 ng/ml anti-CD3, 0.1 ng/ml IL-4 and 50 IU/ml IL-2 at 37° C. and 5% CO2, DN T cells continued to grow. The cells were fed with fresh medium and the exact same concentration of cytokines and anti-CD3 antibody every 3-4 days. The inventors observed that although the peak of DN T cell growth seems to be at day 18, considerable contamination with growing $CD4^+$ $CD8^+$ T cells was also seen at this time point which significantly decreased the purity of the cells (FIG. 6B).

The inventors also examined whether they can use frozen cells as starting population for ex vivo expansion. CD4 CD8-depleted PBMC was frozen in 10% DMSO, 10% RPMI and 80% FBS for at least a week and at most 3 months and thawed rapidly in water bath. After washing twice, cells were counted and cultured the same as described before. The final yield and growth rate of DN T cells was slightly lower than the fresh cells but still within acceptable range (FIG. 6C).

The ability of ex vivo expanded human DN T cells to kill various human tumor cell lines in vitro was assessed. Several human tumor cell lines, including (a) H460SM (matastatic non-small cell carcinoma), (b) H460 (Non Small Cell Carcinoma in b), (c) K562 (Myelogenous Leukemia, (d) A648 (Squamous Cell Carcinoma in c), (e, f) U937 (Histiocytic lymphoma, were labeled with 51Cr and used as targets in standard cytotoxicity assays. Effector cells were purified DN T cells. DN T cells obtained after 10 days of culture as described earlier were first purified by labelling with CD4, CD8 and CD16 monoclonal antibodies attached to MACS® microbeads and incubated at 4° C. for 20 minutes. After washing with PBS plus 0.5% BSA, labelled cells were depleted by passaging the cells through magnetic field using AutoMACS (Miltenyi Biotech) as per manufacturer's instructions. Purity of the obtained DN T cells was then checked by flow cytometry to be more than 95%. Target cells were labelled with 51Cr (100 µCi per 1.0E+6 cells in 100 ul volume) for 45 minutes. After several washings, effector cells were added to 1.0E+3 target cells at ratios indicated in triplicates in 96 well plate. Percent of specific killing was determined by this formula according to chromium release from lysed target cells:

% lysis=[(cpm experimental release−cpm spontaneous release)/(cpm maximal release−cpm spontaneous release)]×100.

Because specific killing of U937 cell line seemed to be saturated at the 10:1-1.25:1 effector:target ratio, the inventors analysed the killing of this tumor cell line by DN T cells at much lower concentration and observed the high capacity of killing even at very low E:T ratios (f).

Figure 7:
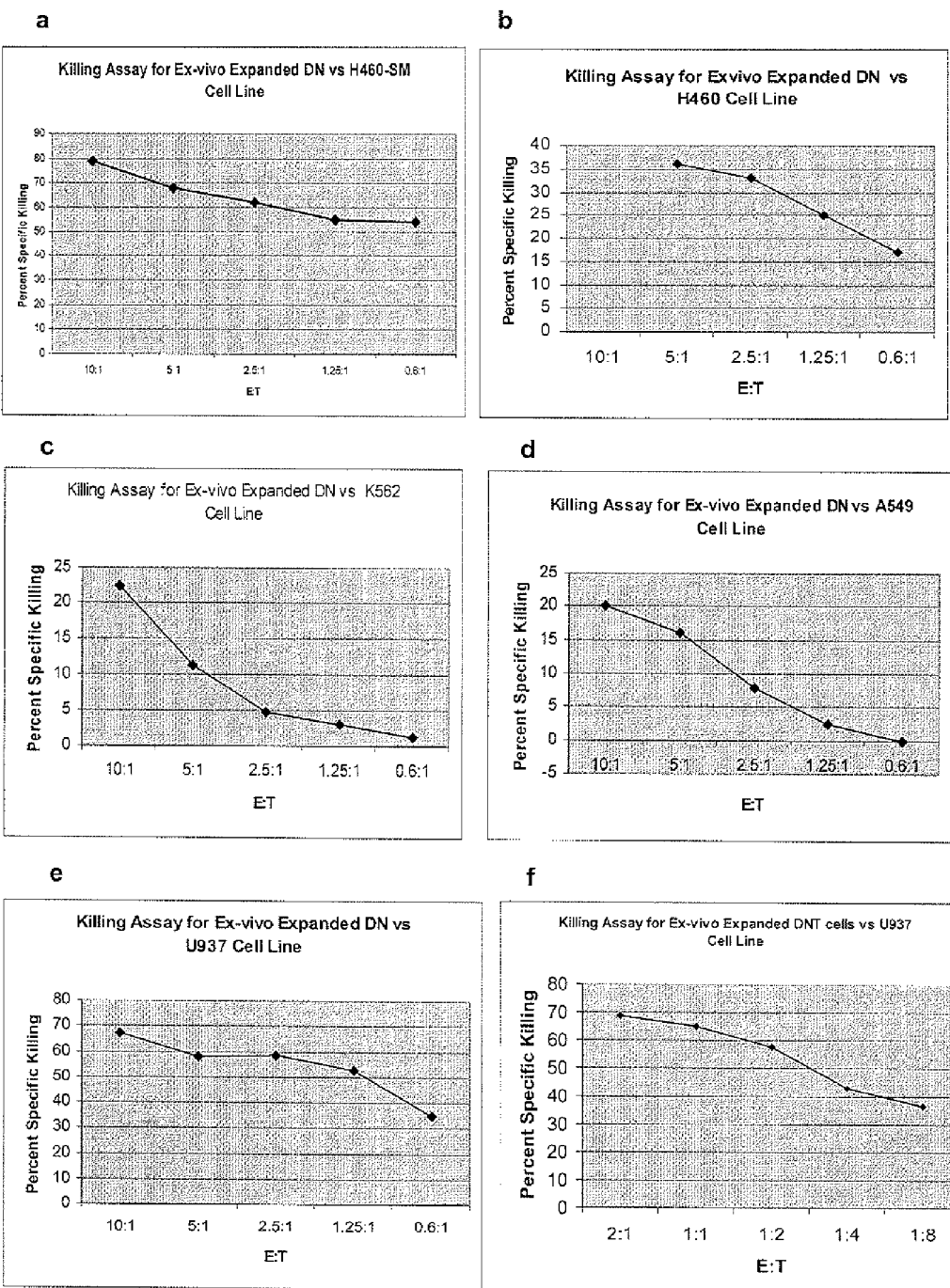
FIGS. 7A-F are graphs showing ex vivo expanded human DN T cells can kill human tumor cell lines in vitro.
Figure 8:
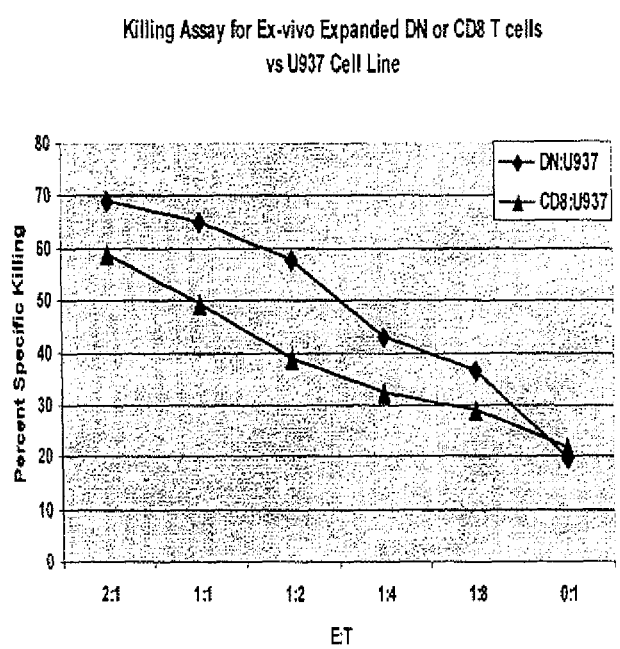
FIG. 8A is a graph showing cytotoxicity of either DN T cells or CD8 T cells against the tumor cell line U937.
FIG. 8B are pictures that visualize cytotoxicity of either DN T or CD8 T cells against tumor cell line H460.
Figure 8:
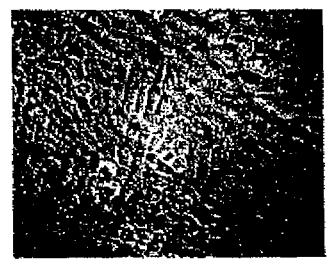
Figure 8:
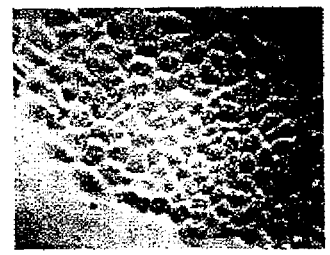
Figure 8:

As shown in FIG. 7A-F, ex vivo expanded human DN T cells could kill these tumor cells very effectively in a dose-dependant manner. 80% of H460SM lung cancer cells were killed at 10:1 effector:target ratio (FIG. 7A), 58% of U937 cells were killed at 1:2 effector:target ration (FIG. 7F). To determine if the ex vivo expanded DN T cells have a stronger anti-tumor effect than CD8$^+$ CTLs that are currently used for adoptive immunotherapy, both DN T and CD8$^+$ T cells were purified from peripheral blood of the same individual and expanded ex vivo. Their ability to kill the human non-small cell lung cancer epithelia cell line NCI-H460 as well as leukaemia cell line U937 was compared. Co-culture of DN T cells with both types of the tumor cell lines resulted in significantly lysis of tumor cells, but CD8 T cells have much less of an effect (FIG. 8A, B). These data indicate that ex vivo expanded human DN T cells are more effective in suppressing and killing tumor targets than conventional CTLs in this model.

Figure 9:
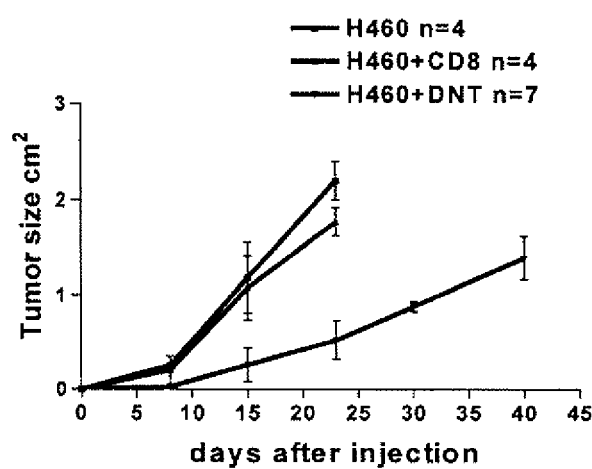
FIG. 9 is a graph showing ex vivo expanded human DN T cells can inhibit human NSCLC (H460 Cell line) progression in SCID mice.
Figure 10:
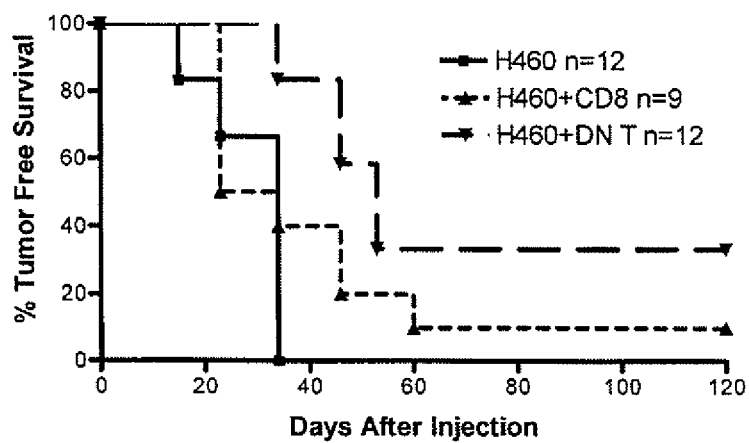
FIG. 10 is a graph showing ex vivo expanded human DN T cells can inhibit human NSCLC progression in SCID mice.

To further determine the anti-cancer effect of human DN T cells in vivo, severe combined immunodeficient (SCID) mice were injected subcutaneously with $10^6$ H460 cells/mouse either alone, or together with $5 \times 10^6$ ex vivo expanded DN T or CD8 T cells. All mice that were injected with H460 cells alone (controls) formed 1.5 cm tumors between 15-34 days after inoculation. This was not significantly affected by co-injection with CD8 T cells. In contrast, tumor growth was significantly delayed in the mice that received a single dose of DN T cells (FIGS. 9-10). The median survival time (MST) of this group was 46 days, which is significantly longer than that of the controls (MST-28.5 days, P=0.01) or CD8 T cell-treated group (MST=34 days, P=0.039). Four of 12 mice treated with DN T cells never developed tumor and remained healthy for more than 4 months (FIG. 10). The results are consistent with those obtained using the mouse DN T cells. Collectively, these studies indicate that ex vivo propagated human DN T cells are more effective in inhibiting human cancer cell growth than that of CD8 T cells both in vitro and in vivo, indicating a potential of using human DN T cells as a novel adoptive cancer immunotherapy. The molecular mechanisms by which human DN T cells inhibit tumor cells are currently under investigation.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR REFERENCES REFERRED TO IN THE SPECIFICATION

1. Blattman J N and Greenberg P D (2004) Cancer immunotherapy: a treatment for the masses. *Science* 305 (5681):200-205.
2. Chen W et al (2005) Donor lymphocyte infusion induces long-term donor-specific cardiac xenograft survival through activation of recipient double-negative regulatory T cells. *J. Immunol.* 175 (5):3409-3416.
3. Chen W H et al (2003) Role of double-negative regulatory T cells in long-term cardiac xenograft survival. *J. Immunol.* 170 (4):1846-1853.
4. Childs R W and Barrett J (2004) Nonmyeloablative allogeneic immunotherapy for solid tumors. *Annu. Rev. Med.* 55:459-475.
5. Curiel T J et al (2004) Specific recruitment of regulatory T cells in ovarian carcinoma fosters immune privilege and predicts reduced survival. *Nat. Med.* 10 (9):942-949.
6. Dudley M E and Rosenberg S A (2003) Adoptive-cell-transfer therapy for the treatment of patients with cancer. *Nat. Rev. Cancer* 3 (9):666-675.
7. Dudley M E et al (2002) Cancer regression and autoimmunity in patients after clonal repopulation with antitumor lymphocytes. *Science* 298 (5594):850-854.
8. Dudley M E et al (2005) Adoptive cell transfer therapy following nonmyeloablative but lymphodepleting chemotherapy for the treatment of patients with refractory metastatic melanoma. *J. Clin. Oncol.* 23 (10):2346-2357.
9. Fischer K et al (2005) Isolation and characterization of human antigen-specific TCR alpha beta+CD4(−)CD8$^-$ double-negative regulatory T cells. *Blood* 105 (7):2828-2835.
10. Fontaine P et al (2001) Adoptive transfer of minor histocompatibility antigen-specific T lymphocytes eradicates leukemia cells without causing graft-versus-host disease. *Nat. Med.* 7 (7):789-794.
11. Ford M S et al (2002) The immune regulatory function of lymphoproliferative double negative T cells in vitro and in vivo. *J. Exp. Med.* 196 (2):261-267.
12. Gattinoni L et al (2005) Acquisition of full effector function in vitro paradoxically impairs the in vivo anti-tumor efficacy of adoptively transferred CD8$^+$ T cells. *J. Clin. Invest* 115 (6):1616-1626.

13. Johansson M and Lycke N (2003) A unique population of extrathymically derived alpha beta TCR+CD4−CD8− T cells with regulatory functions dominates the mouse female genital tract. *J. Immunol.* 170 (4):1659-1666.
14. Khan Q et al (1999) Regulation of apoptosis in mature $\alpha\beta^+$ CD4$^-$CD8$^-$ antigen-specific suppressor T-cell clones. *J. Immunol.* 162:5860-5867.
15. Lan F et al (2001) Allogeneic bone marrow cells that facilitate complete chimerism and eliminate tumor cells express both CD8 and T-cell antigen receptor-alphabeta. *Blood* 97 (11):3458-3465.
16. Leemhuis T et al (2005) A phase I trial of autologous cytokine-induced killer cells for the treatment of relapsed Hodgkin disease and non-Hodgkin lymphoma. *Biol. Blood Marrow Transplant.* 11 (3):181-187.
17. Marijt W A et al (2003) Hematopoiesis-restricted minor histocompatibility antigens HA-1- or HA-2-specific T cells can induce complete remissions of relapsed leukemia. *Proc. Natl. Acad. Sci. U.S.A* 100 (5):2742-2747.
18. Marra L E et al (2004) IL-10 induces regulatory T cell apoptosis by up-regulation of the membrane form of TNF-alpha. *J. Immunol.* 172 (2):1028-1035.
19. Meidenbauer N et al (2003) Survival and tumor localization of adoptively transferred Melan-A-specific T cells in melanoma patients. *J. Immunol.* 170 (4):2161-2169.
20. Perreault C and Brochu S (2002) Adoptive cancer immunotherapy: discovering the best targets. *J. Mol. Med.* 80 (4):212-218.
21. Priatel J J, Utting O, and Teh H S (2001) TCR/Self-Antigen Interactions Drive Double-Negative T Cell Peripheral Expansion and Differentiation into Suppressor Cells. *J. Immunol.* 167 (11):6188-6194.
22. Pure E, Allison J P, and Schreiber R D (2005) Breaking down the barriers to cancer immunotherapy. *Nat. Immunol.* 6 (12):1207-1210.
23. Riddell S R (2004) Finding a place for tumor-specific T cells in targeted cancer therapy. *J. Exp. Med.* 200 (12): 1533-1537.
24. Rosenberg S A et al (1985) Observations on the systemic administration of autologous lymphokine-activated killer cells and recombinant interleukin-2 to patients with metastatic cancer. *N. Engl. J. Med.* 313 (23):1485-1492.
25. Rosenberg S A et al (1988) Use of tumor-infiltrating lymphocytes and interleukin-2 in the immunotherapy of patients with metastatic melanoma. A preliminary report. *N. Engl. J. Med.* 319 (25):1676-1680.
26. Rosenberg S A, Yang J C, and Restifo N P (2004) Cancer immunotherapy: moving beyond current vaccines. *Nat. Med.* 10 (9):909-915.
27. Sasada T et al (2003) CD4$^+$CD25$^+$ regulatory T cells in patients with gastrointestinal malignancies: possible involvement of regulatory T cells in disease progression. *Cancer* 98 (5):1089-1099.
28. Speiser D E and Romero P (2005) Toward improved immunocompetence of adoptively transferred CD8 T cells. *J. Clin. Invest* 115 (6):1467-1469.
29. Toh U et al (2005) Characterization of IL-2-activated TILs and their use in intrapericardial immunotherapy in malignant pericardial effusion. *Cancer Immunol. Immunother.*: 1-9.
30. Turk M J et al (2004) Concomitant tumor immunity to a poorly immunogenic melanoma is prevented by regulatory T cells. *J. Exp. Med.* 200 (6):771-782.
31. Vemeris M R et al (2002) Studies of ex vivo activated and expanded CD8$^+$ NK-T cells in humans and mice. *J. Clin. Immunol.* 22 (3):131-136.
32. Viguier M et al (2004) Foxp3 expressing CD4$^+$CD25 (high) regulatory T cells are overrepresented in human metastatic melanoma lymph nodes and inhibit the function of infiltrating T cells. *J. Immunol.* 173 (2): 1444-1453.
33. Yee C et al (2002) Adoptive T cell therapy using antigen-specific CD8$^+$ T cell clones for the treatment of patients with metastatic melanoma: in vivo persistence, migration, and antitumor effect of transferred T cells. *Proc. Natl. Acad. Sci. U.S.A* 99 (25):16168-16173.
34. Young K and Zhang L (2002) The nature and mechanisms of DN regulatory T-Cell mediated suppression. *Hum. Immunol.* 63 (10):926.
35. Young K J et al (2003a) Inhibition of graft-versus-host disease by double-negative regulatory T cells. *J. Immunol.* 171 (1):134-141.
36. Young K J et al (2001) CD4$^-$CD8$^-$ regulatory T cells implicated in preventing graft-versus-host and promoting graft-versus-leukemia responses. *Transplant. Proc.* 33:1762-1763.
37. Young K J et al (2003b) Antitumor activity mediated by double-negative T cells. *Cancer Res.* 63 (22):8014-8021.
38. Young K J et al (2002) Donor-lymphocyte infusion induces tolerance by activating systemic and graft-infiltrating double negative T regulatory cells. *Blood* 100 (9):3408-3414.
39. Zhang L, Miller R G, and Zhang J (1996) Characterization of apoptosis-resistant antigen-specific T cells in vivo. *J. Exp. Med.* 183:2065-2073.
40. Zhang Z X et al (2000) Identification of a previously unknown antigen-specific regulatory T cell and its mechanism of suppression. *Nat. Med.* 6 (7):782-789.
41. Zou W (2005) Immunosuppressive networks in the tumour environment and their therapeutic relevance. *Nat. Rev. Cancer* 5 (4):263-274.

The invention claimed is:
1. A method for treating a cancer comprising administering an effective amount of a double negative (DN) T cell to a patient in need thereof, wherein the cancer is a leukemia, a lymphoma or lung cancer and wherein the DN T cells are comprised of $\alpha\beta$ and $\gamma\delta$ T cells, and have been made by a process of treating a starting sample comprised of DN T cells or precursors thereof so as to substantially deplete the sample of CD8$^+$ and CD4$^+$ T cells, and wherein the treated sample has further been:
   (a) cultured with an immobilized T cell mitogen in a culture medium comprising an agent that can stimulate DN T cell growth;
   (b) cultured in a culture medium comprising the agent without the T cell mitogen; and
   (c) cultured in culture medium comprising the agent and a soluble T cell mitogen.
2. The method according to claim 1 wherein the T cell mitogen which has been used is an antibody that binds to CD3.
3. The method according to claim 1 wherein the agent which has been used is a cytokine.
4. The method according to claim 3 wherein the cytokine has been selected from IL-2, IL-4, IL-7, 11-12, IL-15 and mixtures thereof.
5. The method according to claim 4 wherein the cytokine comprised IL-2 and IL-4.
6. The method according to claim 1 wherein the starting sample was human peripheral blood.
7. The method according to claim 1 wherein the starting sample was tissue.

8. The method according to claim 1, wherein the sample is treated with antigen prior to being cultured in culture medium with the agent and a soluble T cell mitogen as in step (a).

9. The method according to claim 8 wherein the antigen is the cancer cell or an antigen of the cancer cell.

10. The method according to claim 2 wherein the immobilized T cell mitogen comprised antibodies to CD3 that were coated on a microwell plate, culture bag or flask.

11. A method according to claim 1 wherein the sample was cultured in each of steps (a) through (c) for a period of time from about 1 to about 7 days.

12. The method according to claim 11 wherein in step (b) the cells were cultured for about 3-4 days.

13. The method according to claim 11 wherein in step (a) the cells were cultured for about 3-4 days.

14. The method according to claim 11 wherein in step (c) the cells were cultured for 3-10 days.

15. The method according to claim 1 wherein the starting sample was also substantially depleted of CD56 cells.

16. The method according to claim 1 wherein the starting sample was depleted of $CD8^+$ and $CD4^+$ T cells utilizing antibodies that bind to CD4 and antibodies that bind to CD8.

17. The method according to claim 1, wherein the cancer is a lymphoma.

18. The method according to claim 1, wherein the cancer is a leukemia.

19. The method according to claim 18, wherein the leukemia is acute myelogenous leukemia (AML).

20. The method according to claim 1, wherein the cancer is a lung cancer.

* * * * *